United States Patent [19]

Stanly et al.

[11] 4,318,412
[45] Mar. 9, 1982

[54] ARRANGEMENT FOR CARDIAC ELECTRODE IMPLEMENTATION

[75] Inventors: Albert L. Stanly, Los Angeles; Gunther W. Wimmer, Saugus, both of Calif.

[73] Assignee: Gilbert P. Hyatt, Cypress, Calif.

[21] Appl. No.: 741,917

[22] Filed: Nov. 15, 1976

Related U.S. Application Data

[63] Continuation of Ser. No. 495,091, Aug. 5, 1974, Pat. No. 3,991,747.

[51] Int. Cl.³ .............................................. A61B 5/04
[52] U.S. Cl. .................................................. 128/696
[58] Field of Search ...................... 128/2.06 A, 2.06 B, 128/2.06 E, 2.06 G, 2.06 R, 2.06 V, 2.1 A

[56] References Cited

U.S. PATENT DOCUMENTS 3,478,364 11/1969 Frank ......................... 128/2.06 B X
3,534,727 10/1970 Roman ......................... 128/2.06 E

OTHER PUBLICATIONS

Skutt et al., "IEEE Transactions on Biomedical Engineering", vol. BME-17, No. 4, Oct. 1970, pp. 339–347.

Primary Examiner—William E. Kamm
Attorney, Agent, or Firm—Gilbert P. Hyatt

[57] ABSTRACT

An arrangement is provided for optimizing placement of cardiac electrodes and for improved signal processing. In particular, an arrangement is provided for electrode placement and signal processing to obtain 90% of the information obtained by a 12 electrode electrocardiagram by using an optimun four lead arrangement. Further, this arrangement has additional advantages including convenient access by a user, reduction in muscular artifacts, and other advantages.

3 Claims, 13 Drawing Figures

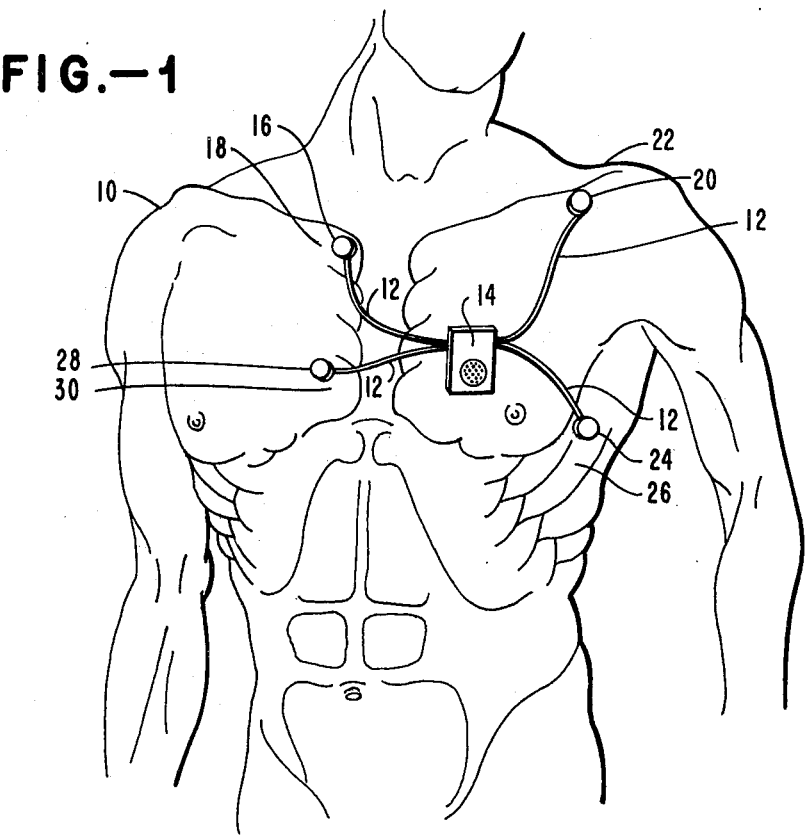
FIG.—1
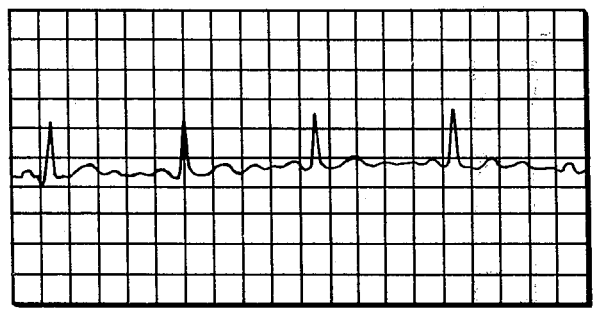
FIG.—2A
STANDARD LEAD I
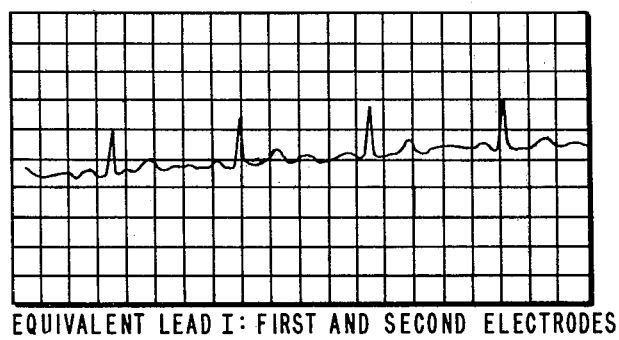
FIG.—2B
EQUIVALENT LEAD I: FIRST AND SECOND ELECTRODES

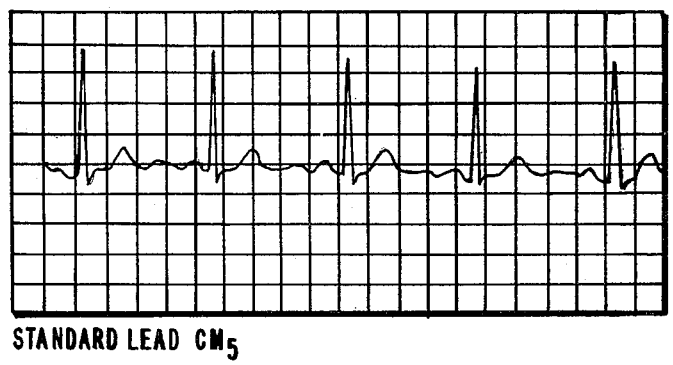
FIG.—3A
STANDARD LEAD $CM_5$
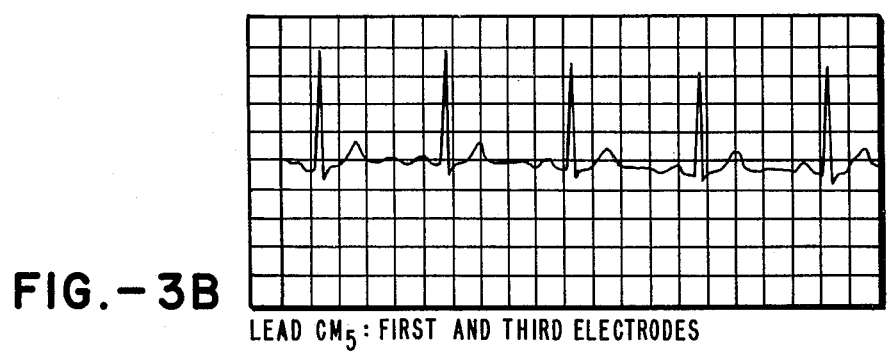
FIG.—3B
LEAD $CM_5$: FIRST AND THIRD ELECTRODES
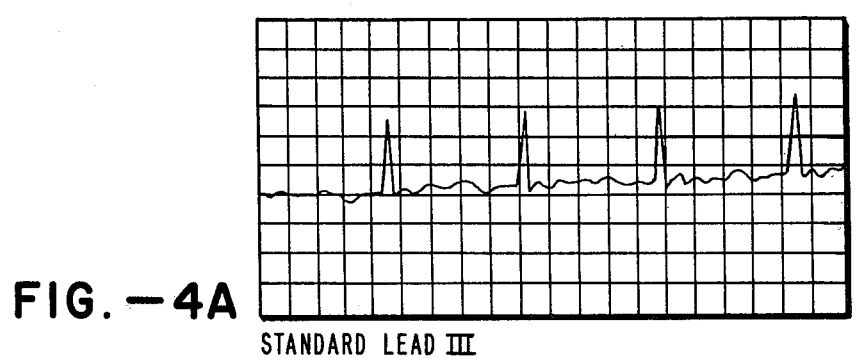
FIG.—4A
STANDARD LEAD III
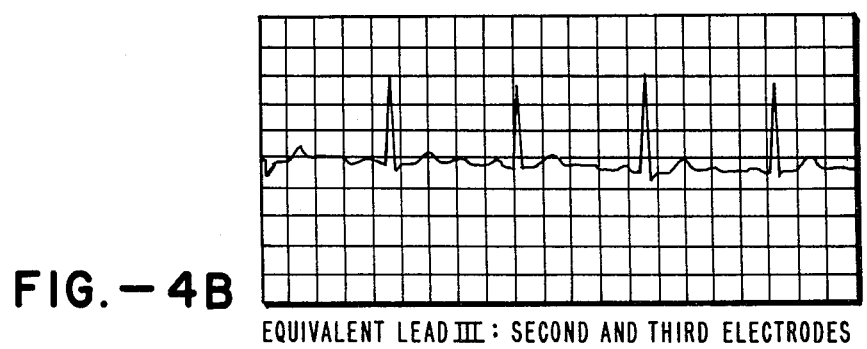
FIG.—4B
EQUIVALENT LEAD III: SECOND AND THIRD ELECTRODES

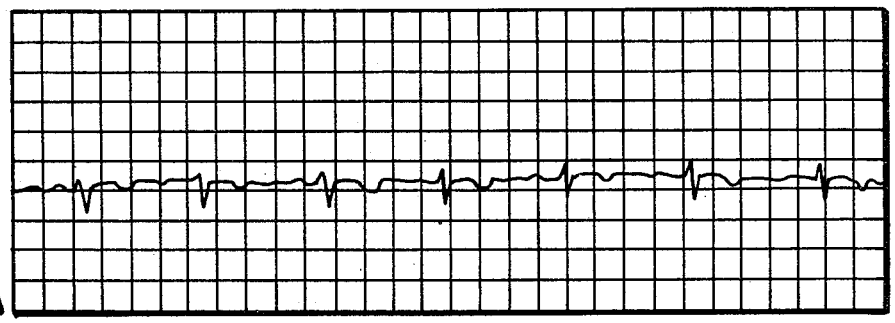
FIG.-5A  STANDARD LEAD $V_1$
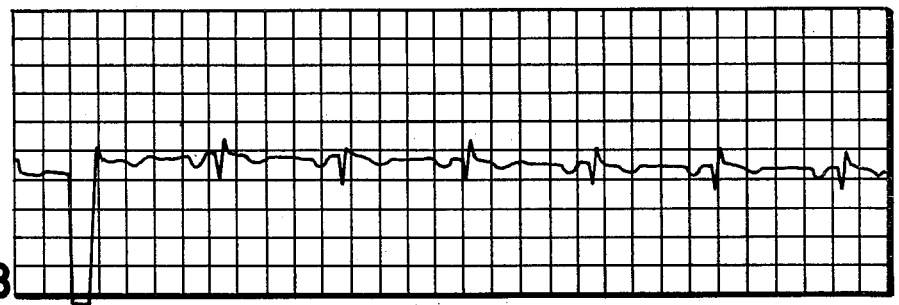
FIG.-5B  ⌐ BATTERY VOLTAGE INDICATION
EQUIVALENT LEAD $V_1$ : SECOND AND FOURTH ELECTRODES
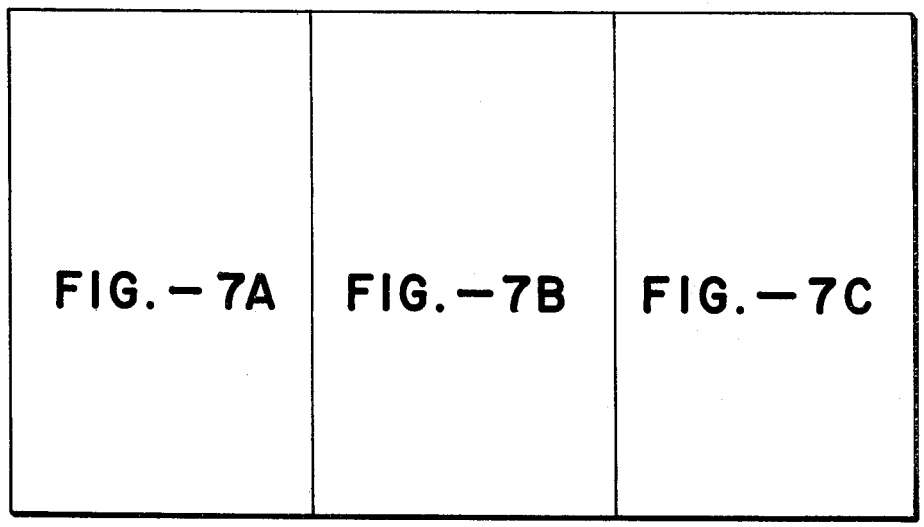
FIG.-6

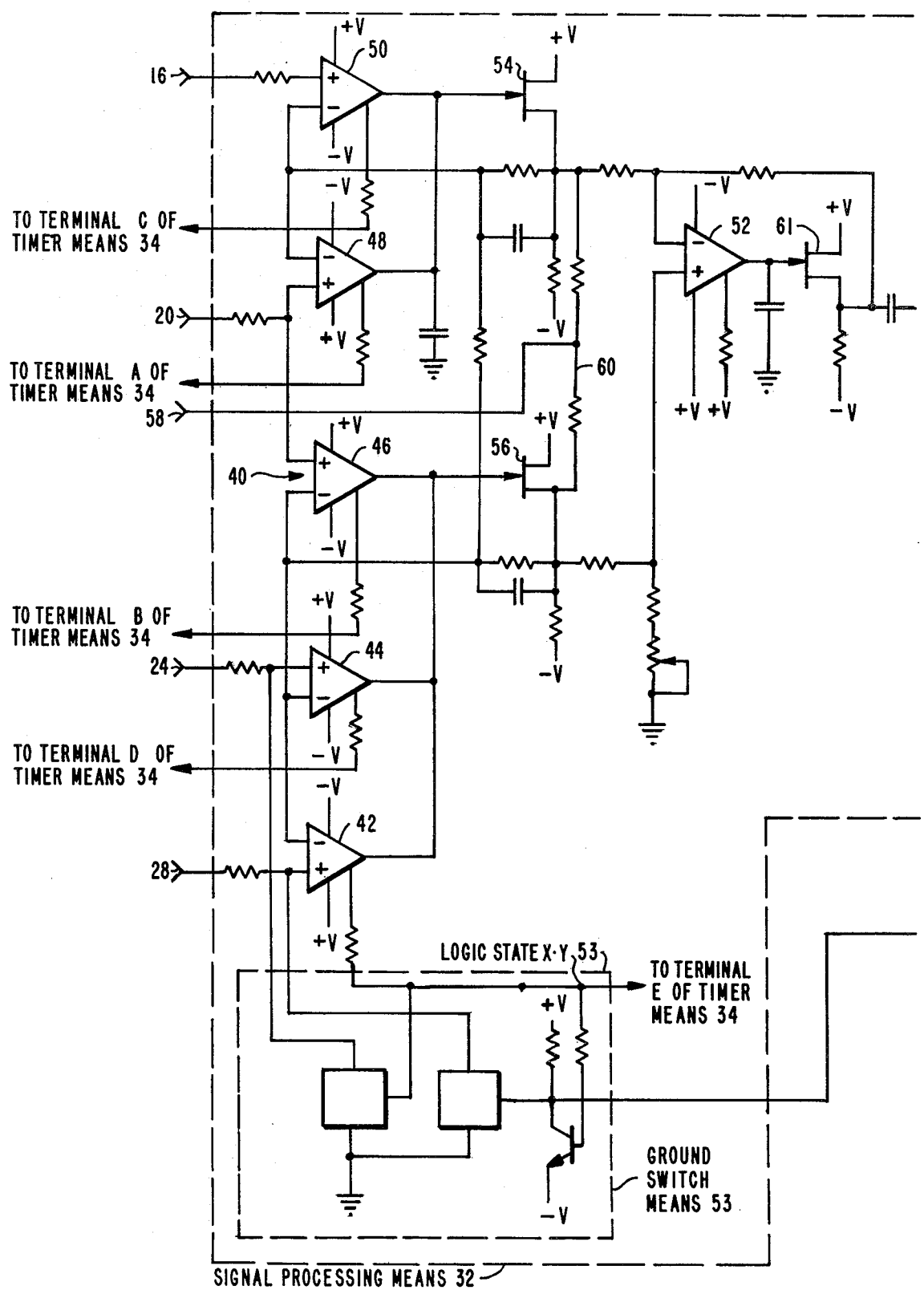
FIG.—7A

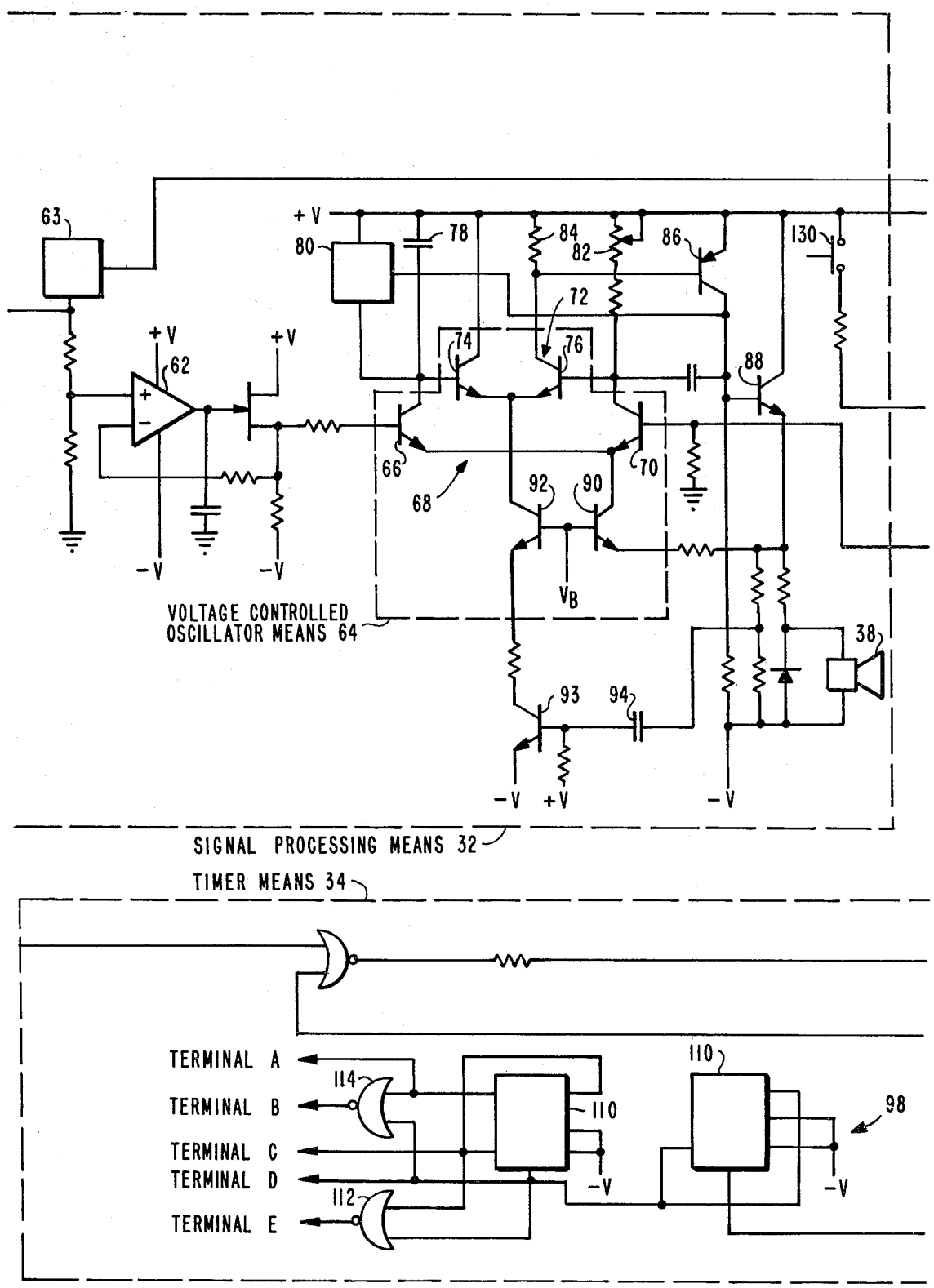
FIG.—7B

ARRANGEMENT FOR CARDIAC ELECTRODE IMPLEMENTATION

CROSS REFERENCE TO RELATED APPLICATIONS

The instant application is a continuation of the patent application noted below in a chain of related applications (1) grandparent application PORTABLE CARDIAC MONITORING SYSTEM Ser. No. 265,473 filed on June 23, 1972 by Stanly et al now abandoned in favor of patent application Ser. No. 495,091 and copending therewith and (2) patent application PORTABLE CARDIAC MONITORING SYSTEM Ser. No. 495,091 filed on Aug. 5, 1974 by Stanly et al now U.S. Pat. No. 3,991,747 issued on Nov. 16, 1976 and copending with said grandparent application and with the instant application wherein the benefit of the filing dates of said grandparent application and said patent application are herein claimed in accordance with the U.S. Code such as with 35 USC 120 and 35 USC 121 and wherein said grandparent application and said patent application are incorporated herein by reference as if fully set forth at length herein.

The instant application is further related to copending application BIOLOGICAL SIGNAL PROCESSING SYSTEM Ser. No. 741,717 filed on Nov. 15, 1976 by Stanly et al.

The relationship of the above referenced applications will become apparent to those skilled in the art from the disclosures therein and the disclosures herein and the wealth of prior art knowledge.

BACKGROUND OF THE INVENTION

1. Field of the Invention

The invention concerns itself with systems and methods for monitoring cardiac action of a patient physically distant from stationary facilities for measuring and analyzing cardiac data.

2. Description of the Prior Art

The value of portable cardiac monitoring devices which sense and transmit cardiac information to distant facilities for processing, display, and analysis has become increasingly recognized. In addition to the many advantages of existing nonportable monitoring devices having the capability of providing cardiac information to distant facilities, such as providing access to sophisticated research and treatment centers and permitting tests to be conducted in physicians' offices, it has been recognized that portable devices would have significant favorable aspects. Such systems may be activated at any time by the user when he senses symptoms of cardiac malfunction or may be operated routinely in accordance with a prescribed program. These functions may be carried out with minimum disruption of the routine of the patient.

There have, however, been many problems in implementing portable cardiac monitoring devices. The stationary monitoring systems are not adaptable to being made portable. These systems generally comprise a standard EKG device equipped with means for transmitting or storing cardiac information for transfer to a distant medical facility. These standard systems are predicated upon isolating the patient from his normal activities and environment. For example, the patient must be isolated from common 60 cycle electrical sources to avoid common mode disturbance of the recorded cardiac signals. The patient must be muscularly relaxed to avoid muscular artifacts in the reading and must be motionless to eliminate error due to static electrical charge. The patient's skin must be specially prepared, usually by abrasion of the epidermal layer, to obviate the problem of artifacts due to variations in skin resistance. Moreover, existing systems utilize a large number of patient contact electrodes interconnected to one another to obtain patterns of cardiac potential related to the conventional EKG data. The interconnections among the electrodes are in some cases through resistors and form a complex network along the patient's body. The expense and bulk of such complex systems have been a substantial problem.

A frequently seen portable system is one having a minimal number of leads to obviate somewhat the problems of unwieldiness and complexity of lead structure of the above-discussed devices. Such simple systems pay a substantial price, however, in diminution of information. Moreover, there has been no significant attack on the problems, which arise particularly frequently with ambulatory patients, of common mode vulnerability and instability of signal due to variations in skin resistance of the patient. Moreover, existing systems suffer from the drawback that the electrodes which they utilize are often affixed over muscle or other tissue and thus introduce muscular artifacts into the sensed potentials from the heart for the non-muscularly relaxed patient. Existing systems further tend to lack the versatility achieved by combining EKG or cardiac monitoring with monitoring of a pacemaker.

Therefore, there has been a recognized but unfulfilled need for a portable cardiac action monitoring system, having the capability of providing substantial cardiac information, as well as pacemaker information, which is not compromised in its ability to process cardiac signals by ambient electrical noise, by fluctuations in skin resistance of the patient or by muscular artifacts and is at the same time economical and sufficiently comfortable, convenient, compact, and lightweight to meet the physical and social needs of ambulatory patients utilizing the device. Monitoring systems which fulfill these requirements must also, if possible, provide transmittable signals for conventional communications systems (e.g. telephones) that can be used after demodulation for recordation by conventional means, such as an EKG recorder or tape recorder.

SUMMARY OF THE INVENTION

Systems and methods are provided for monitoring the cardiac and pacemaker action of a patient, physically removed from stationary facilities for measuring and analyzing cardiac data. The system which is compact, lightweight, and readily portable, includes a plurality of electrodes conveniently affixable to the chest region of the patient at selected, bony portions thereof to sense potentials generated in conjunction with the patient's cardiac action. The electrodes are arrayable in the X, Y and Z planes so that potentials sensed by selected bipolar pairs of a total of no more than four electrodes provide a very large percentage (up to 90%) of the information obtainable by conventional 12 lead EKG techniques as well as some of the critical precordial leads. The electrodes, which are not connected to one another across the body of the patient, are electrically connected to signal processing means for combining and preparing signals, generated by the potentials sensed by selected pairs of electrodes, for serial or multiplex transmission to a distant facility. The characteristic spike of the pacemaker potential can be readily extracted from a composite signal and provides a test of the effectiveness and remaining life of the pacemaker battery. Means are also provided for maintaining a selected signal for as long an interval as desired.

The signal processing means is of very high electrical impedance in relation to the impedance of the patient and thus minimizes errors and artifacts due to fluctuations in skin resistance of the patient, thereby obviating the need for preparatory treatment of the skin of the patient. The signal processing means includes a sequential control for processing currents derived from the potentials sensed by the electrodes in selected pairs, for selected intervals. The signal sequence is modulated for multiplex transmission—by radio, telephone, or other convenient means—of the combined electrode pair or lead readings. The serially presented data contain substantially 90% of the data available from the conventional EKG.

Switch settling means included in the signal processing means permits rapid switching between electrode pairs. The signal processing means further includes means for selectively grounding one of the non-accessed electrodes during each period of conduction of the selected electrode pairs, providing a common DC return to the patient.

The potential of the power source, a DC battery, is reflected in a separate signal transmitted as a marker, within the cycle of lead switching. Approaching end of battery life is indicated by a sharply defined and easily discernible change in the battery signal.

Particular elements in the signal processing means contribute to sensitivity, stability and high impedance operation of the system. Signals from pairs of electrodes pass through buffer amplifiers which are selectively activated to permit signal conduction into the signal processing system, through a differential amplifier to a voltage controlled oscillator (VCO) arranged as an FM modulator, the modulated signals driving a speaker. The buffer means input impedance is enhanced by coupled field effect devices which act as source followers thus significantly reducing the load on the buffer imposed by subsequent circuitry. The VCO means, which is highly sensitive and stable, also contributes to high impedance operation. The VCO means comprises matched pairs of differential amplifiers regeneratively connected to amplifying transistor elements. Aspects of circuitry and operation such as timesharing and sequenced use of circuit elements contribute to substantial economies. Means are provided for suppression of VCO frequencies which interact adversely with telephone systems.

BRIEF DESCRIPTION OF THE DRAWINGS

FIG. 1 is a perspective view of a plurality of electrodes in electrical contact with a patient and coupled to a signal processing system in accordance with the invention;

FIGS. 2A–5B are simplified graphical recorder charts (designated A) of cardiac action obtained from conventional EKG measurement, as compared to equivalent charts (designated B) of cardiac action obtained by measurements in accordance with the invention;

FIG. 6 is a diagram of the manner in which the various circuit portions of FIGS. 7A, 7B and 7C join together to form a complete circuit; and FIGS. 7A, 7B and 7C, taken together, comprise a shematic circuit diagram of a cardiac monitoring system in accordance with the invention.

DETAILED DESCRIPTION OF THE INVENTION

Figure 7C:
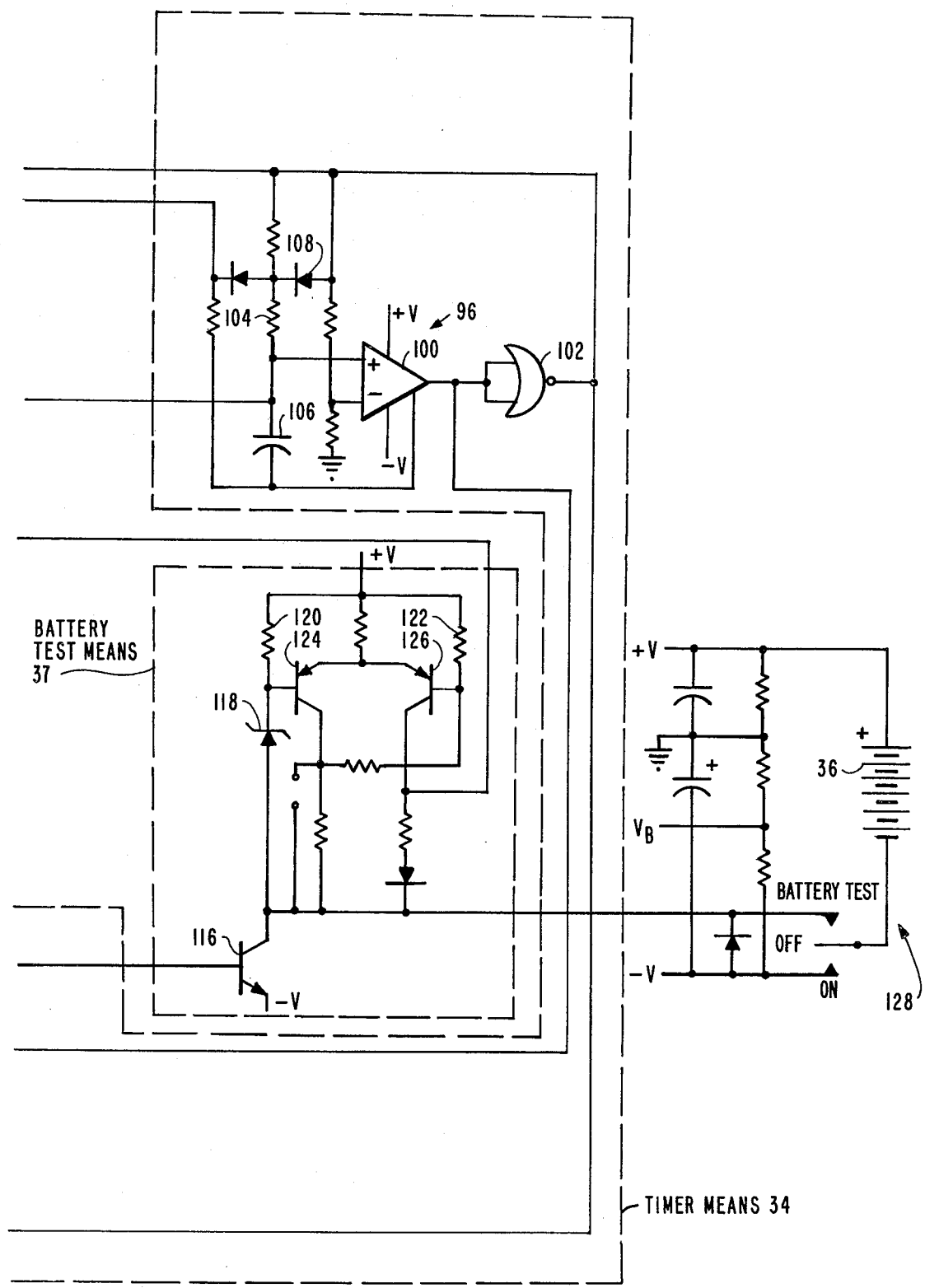

A plurality of electrodes are affixed at selected positions on the chest of an ambulatory patient to sense potentials due to cardiac or pacemaker action of the patient, for transmission by radio, telephone or other means to an EKG and pacemaker performance measuring and analyzing facility. The electrodes are connected to timing, control and signal processing means contained in a small, conveniently worn or stored housing. Signals from sequenced, selected combination of electrodes are serially transmitted for given intervals after modification, and in the case of telephone transmission are converted to audio output. The pairs of electrodes are so arrayed as to yield substantially all the data, from as few as four electrodes connected to provide bipolar leads, obtainable from the conventional 12 lead EKG. The signal processing system includes highly sensitive and stable circuit elements providing low current, very high impedance operation and minimizing variations and limitations imposed by electrode attachment, as well as minimizing local variation in skin resistance of the patient and common mode operation with conventional electrical sources. Means are provided for processing and transmitting a power source signal as a marker and as an indication of the effectiveness and remaining useful life of the power source which may comprise an ordinary flashlight battery. Where a pacemaker is used, the transmitted signals are in a form to provide data for evaluation of the pacemaker effectiveness. At the receiving end, the transmitted signals are recorded or displayed on an EKG recorder, tape recorder, oscilloscope, or heart-pacer condition readout apparatus.

As shown in FIG. 1, a plurality of electrodes are attached in electrical contact with the body 10 of a patient, and each is coupled by a conductor 12 to a small battery-powered cardiac monitor 14 in accordance with the invention. A first electrode 16 is affixed to the right side of the manubrium 18 of the patient. A second electrode 20 is affixed to the outer left clavicle 22 of the patient. A third electrode 24 is attached in the area of the "$V_5$ position" along the ribs 26 of the patient. The $V_5$ position is recognized in medical terminology as a specific rib position and this designation is used hereafter. A fourth electrode 28 is affixed to the patient in the area of the "$V_1$ position" 30, conventionally used to designate the right side of the sternum, fourth rib. The electrodes are thus arrayed in the X, Y and Z planes. (In the medical profession the human chest is considered as having X, Y and Z planes for purposes of EKG connection. The X and Y axes of such a coordinate system are considered as extending across the width and along the height of the chest respectively, while the Z axis extends into the chest.) It should be noted that, of course, the positions of the electrodes could be altered by, for example, substituting the $V_2$ or $V_3$ positions for the $V_1$ position or by disposing the first and second electrodes at other points to the right and left, respectively, of the upper sternum.

FIGS. 2A-5B are comparative graphical recorder outputs taken for various electrode pairs with conventional systems and systems in accordance with the invention. As shown in FIG. 2, the graph of the signal representing the difference in potential between the first electrode 16 and the second electrode 20 (FIG. 2B) corresponds closely to the output (FIG. 2A) provided by the conventional horizontal first lead (standard lead I) of the standard electrocardiogram. (In the medical profession the term "lead" means "a signal generated by one 'exploring' electrode and one or a combination of other electrodes"; for example, many of the classical EKG "leads" comprise three electrodes connected in parallel to yield a signal in conjunction with a fourth electrode; the term is frequently used in this manner herein as determined from the context).

The difference in potential between the first electrode 16 and the third electrode 24 (FIG. 3B) comprises the known $CM_5$ lead (FIG. 3A) sometimes used in stress testing (the manubrium to $V_5$ position) and provides further information comprising substantially 90% of the ischemic indications on the standard 12 lead EKG. This lead provides a combination of the anterior-posterior lead $V_5$ and the transverse vertical-horizontal lead $aV_F$. The difference in potential between the second and third electrodes 20, 24 (FIG. 4B) provides information equivalent to that provided by the conventional vertical EKG lead III (FIG. 4A). The potential difference between the second electrode 20 and the fourth electrode 28 provides an anterior-posterior reading closely equivalent to the conventional $V_1$ lead (FIGS. 5A, 5B). The fourth electrode 28 could be moved to the $V_2$ or $V_3$ positions and would yield anterior-posterior cardia data together with significant precordial information. Thus, each of the first three electrodes performs as an element of two different leads, and the information obtainable from the electrode array is consequently varied, extensive, and significant.

The various electrode combinations provide over approximately 90% of the ischematic indications normally shown in a complete 12 lead EKG record. The second-fourth electrode combination provides an excellent means for determining atrial disorders and for distinguishing between ventricular atrophy and aberration. Thus in accordance with the invention a convenient array of a relatively small number of electrodes provides information substantially equivalent to that provided by the conventional EKG system, which employs a complex and cumbersome network of electrodes. All the electrodes can be affixed over bony portions of the body of the patient and thus are not subject to sensing irregular potentials due to muscular artifacts which obscure, sometimes to a considerable degree, the cardiac data desired. The electrodes are placed on the patient's body so that they are conveniently accessible to the patient.

The internal circuitry of cardiac monitor 14 (FIG. 1) is shown in FIGS. 7A-7C which are connected together in the form shown in FIG. 6.

The circuitry shown in FIG. 7A will now be discussed in detail.

As shown in FIG. 7A, the electrodes are connected to signal processing means 32, which amplifies and otherwise prepares electrical currents due to the potentials sensed by the electrodes for transmission to a distant facility having the capability of graphing and analyzing the cardiac data from the patient. The signal processing means 32 has very high impedance in relation to the impedance of the patient, typically 2,000 megohms at 1 cps and 500 megohms or more at 120 cps as compared with 150,000 ohms or less for the patient. Thus, variations in skin resistance of the patient have little or no effect on the graphical record of the patient's cardiac data.

Timer means 34 is connected to the signal processing means 32 and provides signals to the signal processing means 32 so that the means 32 is conductive with respect to selected pairs of electrodes for selected time intervals and in a chosen sequence to form a complete cycle for multiplex transmission. For example, a practical sequence is Lead I (second electrode minus first electrode), Lead III (third electrode minus second electrode), Lead $CM_5$ (third electrode minus first electrode), and $V_1$ lead (fourth electrode minus second electrode). A DC power source 36 in the form of a battery is coupled to the signal processing means 32.

At a preselected point in the multiplex cycle the timer means 34 provides a signal activating sync or battery test means 37 to provide a signal to the signal processing means 32. This permits a sync or battery test impulse to pass through the signal processing means 32 to the recording facility. The battery impulse graph thus acts as a marker to determine where in the cyle transmission is begun to be recorded as well as providing a means for monitoring the effectiveness of the battery.

The timer means 34 further provides signals to the signal processing means 32 so that at any time when the signal processing means is conductive for a pair of electrodes one of the remaining, nonconductive electrodes acts as a ground which, through the patient, provides bias potential for elements at the input of means 32 and thus facilitates high input impedance as noted below.

The signal processing means 32 contains electronic elements for processing currents due to the differences in potentials between given pairs of electrodes for transmission via a speaker 38 and a transmitter to a distant recording and analyzing facility. Under the influence of the timer means 34, pairs of a plurality of buffer amplifiers 40 included in means 32 are activated to be conductive with respect to currents from selected pairs of the electrodes 10. In the particular configuration shown there are five buffers; a first buffer 42 connected to the fourth electrode 28, a second buffer 44 connected to the third electrode 24, a third buffer 46 connected to the second electrode 20, a fourth buffer 48 connected to the second electrode 20, and a fifth buffer 50 connected to the first electrode 16. In the particular configuration shown herein, whenever the signal processing means 32 is receiving current from the electrodes 10, one of the buffers 42, 44, 46 is on and one of the other two buffers 48 and 50 is also on. The first, second and third buffers 42, 44, 46 buffer signals entering the non-inverting end of a differential amplifier 52; the fourth and fifth buffers 48, 50 buffer signals entering the inverting end of the amplifier 52.

For purposes of exposition, the currents due to potentials sensed by the first electrode 16 and the second electrode 20 will be specifically considered. These currents exist when the timer means 34 activates buffers 46, 50 to conduct current to the signal processing means 32. At the same time, ground switch means 53 is activated so that the fourth electrode 28 acts as ground. The currents from the first and second electrodes 16, 20 pass to field effect transistors 54, 56, respectively, where the currents provide bias. The field effect transistors 54, 56 are connected between plus and minus potential sources (±V). In effect the field effect transistors 54, 56 at this time comprise functional elements of buffer combinations including the buffers 46, 50 respectively. The field effect transistors, in this view, act as effective outputs for their respective buffers. The field effect transistors operate at high gain with very low input current in contrast, for example, to a junction type transistor. Thus, the field effect transistors optimize the high impedance characteristics of the buffers and enable the high impedance of the signal processing means 32 to exist without sacrifice of gain or accuracy. In a typical example, the gain times open loop impedance of the signal processing means is 2,000 megohms.

The outputs of the field effect transistors 54, 56, are connected to the differential amplifier 52. A well known prior art shielded cable is used to connect the buffer amplifiers and the electrodes on the patient, where a shield encloses the signal wires. The signal wires are connected to terminals 16, 20, 24, and 28 and the shield is connected to terminal 58 (FIG. 7A). The shield connection is used to protect the system from common mode signals. The effect of the capacitance between the shield and wires is negated by a voltage divider 60 to which the shield and the buffer inputs are connected. The shield and the input wires are consequently at the same potential, thus neutralizing the effect of the capacitance between the shield and wires.

The circuitry shown in FIGS. 7B and 7C will now be discussed in detail.

The effective output of the differential amplifier 52, field effect transistor means 61 is coupled to interstage buffer means 62 and analog switch 63, which is excited by timer means 34 to faciliate rapid settling of signals following switching of electrode pairs.

The output of interstage buffer amplifier 62 is connected to a voltage controlled oscillator means 64 and specifically to the base of a first transistor 66 of a first transistor pair 68 of the VCO 64. The VCO provides further gain with high inherent sensitivity and stability. Substantial economies are achievable through the use of the VCO arrangement shown vis-a-vis the more conventional integrating capacitors or operational amplifiers which could be used for the same purpose. A second transistor 70 is included in the first differential amplifier pair 68. A second differential amplifier pair 72 is included in the VCO 64 and comprises first and second transistors 74, 76 whose bases are coupled to the collectors of the first differential amplifier pair 68. The collector of transistor 66 is also coupled to a pair of parallel circuit elements, a capacitor 78 and an analog switch 80, as is the base of the transistor 74. The collector of transistor 70 is coupled to a resistor 82 as is the base of transistor 76. Coupled to the collector of transistor 76 are a resistor 84 and the base of PNP means 86. The collector of PNP means 86 connects to the analog switch 80. The elements 74, 76, 78, 80, and the combination of elements 82, 84, and 86 are connected in parallel to the source of positive potential 36. Also in parallel with these elements is NPN means 88, whose base is connected with analog switch 80 and with the collector of PNP means 86.

The emitter of NPN means 88 connects to speaker 38, whose output is coupled to a transmission means (not shown), and to transistor means 90 whose collector is coupled to the emitters of the first differential amplifier pair 68. Transistor means 92 is coupled at its base to the base of transistor 90 and to a bias voltage, V, and at its collector is coupled to the emitters of the second differential amplifier pair 72. The emitter of transistor 92 is coupled to a transistor 93 and a differentiating capacitor 94 coupled thereto, which together comprise a strobe means for suppressing frequencies adverse to telephone networks (above 2450cps).

In operation, when only current due to the voltage source and sink exist in the VCO an emitter current is established at the terminals of the first differential amplifier pair 68 and is equally shared at the terminals. The current charges capacitor 78 and passes through resistor 82. When the potentials at the terminals are equal and the hold off period of the strobe, which operates as a one-shot, has elasped, the second differential pair 72 senses the equality and provides bias current to PNP means 86. The PNP means 86 responds with current to NPN means 88 which provides current to drive the speaker 38, simultaneously removing emitter current of differential pair 68 through transistor 90 and providing a regenerative effect due to to collapse of the established potential of resistor 82. Current is provided to the differentiating capacitor 94 to restore the potential required for a subsequent cycle. During this time capacitor 78 tends to retain its charge while resistor 82, of course, does not and thus in differential pair 72 current imbalance is produced which provides positive feedback. The analog switch 82 is set to discharge the capacitor 78 to a predetermined voltage to reset the cycle.

When there is modulation, that is when a cardiac potential difference signal is received from the interstage buffer amplifier 62, an imbalance is created in the emitter currents at the terminals of the first differential amplifier pair 68 producing differential charging of the capacitor 78 and thus a gain which drives the speaker 38. Therefore, signals are transmitted as deviations from a base signal.

The timer means 34 includes a free running multivibrator 96 and a counter 98. The multivibrator 96 clocks the counter 98 and in a typical application provides an eight second delay and a 0.2 second pulse so that, every eight seconds, a pulse of 2/10th second duration occurs. The leading edge of the pulse increments the counter. An amplifier 100 of the multivibrator 96 drives a gate 102 which functions to increase ($\Delta V/\Delta T$) of the transition time. The timing is accomplished by series-connected resistor means 104 and capacitor means 106. The amplifier 100 operates effectively as a voltage comparator, and the pulse is applied to the effective negative terminal on the amplifier. The effective positive terminal of the amplifier in effect operates as a voltage divider operating at 50% of the applied voltage or 0.7 of one time constant per RC. Diode means 108, connected to the inverting end of the amplifier 100, bypasses the resistor means 104 to permit deviation from a symmetrical square wave.

The counter 98 operates as a ripple counter and includes a pair of flip flops 110 connected as primary and slave flip flop or memory. The two flip flops thus comprise a four state ripple counter with the second state being derived from the terminal outputs of the first state. The states are decoded by gates 112, 114 and the appropriate current is applied to the input buffers 40 corresponding to the desired logic state. In the specific embodiment shown, terminals A, B, C, D, and E couple to the buffers 40 as follows: terminal A (corresponding to logic state Y of the counter 98) to buffer 48; terminal B (logic state $X\overline{Y}$) to buffer 46; terminal C (logic state $\overline{Y}$) to buffer 50; terminal D (logic state $\overline{X}$) to buffer 44; and terminal E (logic state XY) to buffer 42. Terminal E also couples to the ground switch 53 which closes at logic state XY and $\overline{XY}$. This permits grounding of one non-accessed electrode during conduction by each selected pair of electrodes. Thus, four distinct logic states exist corresponding to the four different cardiological leads described above. Each pair transmits for eight seconds per cycle with approximately 2/10th of a second reset time during which the non-symmetrical square wave is applied to the means 63 to effect switch settling.

At a selected point in the cycle a sync or battery test signal is transmitted. This signal acts as a marker as well as an indicator of approaching end of life for the battery and, in the depicted system, is generated during the reset pulse preceding the fourth count as seen in FIG. 5B. Through gate 112, the fourth logic state of the counter 98 activates the battery test means 37. The battery test means 37 comprises a saturable switch transistor 116 which drives a voltage reference zener diode 118 and an adjustable voltage divider comprising resistors 120, 122. The resistors are connected to a differential pair of transistors 124, 126. Transistor 126 is connected to the base of transistor 70 in the VCO 64. The battery test is performed at twice nominal load in order to verify battery impedance.

The voltage divider is adjusted so that, if the battery voltage should fall below a predetermined value—7.4 volts in a specific example—current will pass to the transistor 70 and thus cause the output frequency to decrease. Conversely, when the voltage is above the preselected value, current would be drawn from the base of transistor 70 and the output frequency would increase, indicating an acceptable battery condition. The system may be arranged so that the battery test signal is audible to the patient.

A local battery test feature is provided to permit the patient to test the battery at any point in the cycle. In a power switch means 128, there are three positions of a power switch, "on", "off", and "battery test". The battery test terminal connects the (−) terminal of the battery to the zener diode 118 so that upon activation of the battery test terminal of the power switch the battery test impulse overrides all other signals to the VCO.

Also provided in accordance with the invention are means for continuing the transmission of desired signals from a given pair of electrodes beyond the time allotted to that electrode pair in the cycle of lead switching provided herein. A hold switch 130 is disposed between +V and the timer 96 so that one lead is connected at the output of capacitor 106 and the other is connected to the voltage means 36. When closed, the switch 130 disables the timer so that no lead switching can occur. This feature is advantageous for use in response to a request from the distant EKG analysis facility for further cardiac signal transmission from a particular lead.

In accordance with the invention, the action of a pacemaker affixed to the patient may be monitored. The periodicity of the pacemaker impulse and the time interval between the impulse and ventricular activation are both indications of pacemaker effectiveness. The pacemaker spike impulse is distinctive and can be readily recognized within, and separated from cardiac data transmitted by systems in accordance with the invention; thus, the effectiveness of the pacemaker can be readily monitored.

At the distant center to which the cardiac action signals are transmitted, the signals are received, demodulated, and displayed by conventional means (not shown). The display may be by oscilloscope, magnetic tape, EKG recorder, pacemaker condition displays, or other standard display means.

The described embodiments contribute specific examples of systems in accordance with the invention and do not by themselves limit the invention, which is defined by the following claims.

What is claimed is:

1. A four electrode biological monitoring system comprising:
   a manubrium electrode for generating a manubrium position related signal;
   a clavicle electrode for generating a clavicle position related signal;
   a $V_5$ position electrode for generating a $V_5$ position related signal;
   a $V_1$ position electrode for generating a $V_1$ position related signal; and
   signal processing means for generating a processed output signal in response to the manubrium position related signal, the clavicle position related signal, the $V_5$ position related signal, and the $V_1$ position related signal; wherein said signal processing means includes means for generating a $CM_5$ lead related signal in response to the manubrium position related signal and the $V_5$ position related signal.

2. A four electrode biological monitoring system comprising:
   a manubrium electrode for generating a manubrium position related signal;
   a clavicle electrode for generating a clavicle position related signal;
   a $V_5$ position electrode for generating a $V_5$ position related signal;
   a $V_1$ position electrode for generating a $V_1$ position related signal; and
   signal processing means for generating a processed output signal in response to the manubrium position related signal, the clavicle position related signal, the $V_5$ position related signal, and the $V_1$ position related signal; wherein said signal processing means includes means for generating a vertical EKG lead III related signal in response to the clavicle position related signal and the $V_5$ position related signal.

3. A four electrode biological monitoring system comprising:
   a manubrium electrode for generating a manubrium position related signal;
   a clavicle electrode for generating a clavicle position related signal;
   a $V_5$ position electrode for generating a $V_5$ position related signal;
   a $V_1$ position electrode for generating a $V_1$ position related signal; and
   signal processing means for generating a processed output signal in response to the manubrium position related signal, the clavicle position related signal, the $V_5$ position related signal, and the $V_1$ position related signal; wherein said signal processing means includes means for generating a $V_1$ lead related signal in response to the clavicle position related signal and the $V_1$ position related signal.

* * * * *